(12) United States Patent
DeNatale et al.

(10) Patent No.: US 7,328,604 B2
(45) Date of Patent: Feb. 12, 2008

(54) MICROELECTROMECHANICAL (MEM) FLUID HEALTH SENSING DEVICE AND FABRICATION METHOD

(75) Inventors: Jeffrey F. DeNatale, Thousand Oaks, CA (US); Robert L. Borwick, III, Thousand Oaks, CA (US); Philip A. Stupar, Oxnard, CA (US); Martin W. Kendig, Thousand Oaks, CA (US)

(73) Assignee: Teledyne Licensing, LLC, Thousand Oaks, CA (US)

( * ) Notice: Subject to any disclaimer, the term of this patent is extended or adjusted under 35 U.S.C. 154(b) by 230 days.

(21) Appl. No.: 11/234,015

(22) Filed: Sep. 22, 2005

(65) Prior Publication Data

US 2007/0062261 A1 Mar. 22, 2007

(51) Int. Cl.
*G01N 11/00* (2006.01)
(52) U.S. Cl. .................. 73/54.02; 73/54.01; 73/53.01
(58) Field of Classification Search ............. 73/54.02, 73/54.01, 53.01
See application file for complete search history.

(56) References Cited

U.S. PATENT DOCUMENTS

| | | | |
|---|---|---|---|
| 4,176,545 A | 12/1979 | Oddo | 73/64 |
| 5,025,346 A | 6/1991 | Tang et al. | 361/283 |
| 5,444,367 A | 8/1995 | Kempster et al. | 324/204 |
| 6,159,385 A | 12/2000 | Yao et al. | 216/2 |
| 6,196,057 B1 * | 3/2001 | Discenzo | 73/54.01 |
| 6,286,363 B1 * | 9/2001 | Discenzo | 73/53.01 |
| 6,324,899 B1 * | 12/2001 | Discenzo | 73/53.05 |
| 6,463,796 B1 | 10/2002 | Van Mullekom et al. | 73/118.1 |
| 6,471,853 B1 | 10/2002 | Moscaritolo | 210/85 |
| 6,644,095 B2 | 11/2003 | Van Mullekom et al. | 73/10 |
| 6,852,216 B2 | 2/2005 | Moscaritolo et al. | 210/85 |
| 7,024,920 B2 * | 4/2006 | Discenzo | 73/53.05 |
| 7,104,116 B2 * | 9/2006 | Discenzo | 73/54.28 |
| 2004/0027029 A1 | 2/2004 | Borwick, III et al. | |
| 2004/0113513 A1 | 6/2004 | Borwick, III et al. | |
| 2005/0066711 A1 * | 3/2005 | Discenzo | 73/64.56 |
| 2006/0010964 A1 * | 1/2006 | Sparks et al. | 73/54.01 |

(Continued)

OTHER PUBLICATIONS

"Microfluidics Meets MEMS", Proceedings of the IEEE, vol. 91, No. 6, Jun. 2003, pp. 930-953.

(Continued)

*Primary Examiner*—Hezron Williams
*Assistant Examiner*—Rodney Frank
(74) *Attorney, Agent, or Firm*—Koppel, Patrick, Heybl & Dawson

(57) ABSTRACT

A microelectromechanical (MEM) fluid health sensing device comprises a viscosity sensor which provides an output that varies with the viscosity of a fluid in which it is immersed, and at least one other sensor which provides an output that varies with another predetermined parameter of the fluid. The viscosity sensor is preferably a MEM device fabricated by means of a "deep etch" process. The sensors are preferably integrated together on a common substrate, though they might also be fabricated separately and packaged together to form a hybrid device. A data processing means may be included which receives the sensor outputs and provides one or more outputs indicative of the health of the fluid. Sensor types which may be part of the present device include, for example, a temperature sensor, a MEM electrochemical sensor, a MEM accelerometer, a MEM contact switch lubricity sensor, and/or an inductive metallic wear sensor.

47 Claims, 4 Drawing Sheets

U.S. PATENT DOCUMENTS

2006/0065045 A1* 3/2006 Borwick et al. ........... 73/54.23
2006/0169033 A1* 8/2006 Discenzo ................... 73/64.56
2007/0054433 A1* 3/2007 DeNatale et al. ............. 438/48

OTHER PUBLICATIONS

"Presettable Micromachined MEMS Accelerometers", Proceedings of the 12th IEEE International Conference on Micro Electro Mechanical Systems (MEMS'99).

"A Single-crystal Silicon 3-axis CMOS-MEMS Accelerometer," IEEE Sensors 2004, Vienna, Austria, Oct. 2004.

"MEMS Sensors for HVAC&R", ASHRAE Journal, May 2004, pp. 69-74.

"A hybrid approach to low-voltage MEMS switches," TRANSDUCERS '03, 12th International Conference on Solid-State Sensors, Actuators and Microsystems, Digest of Technical Papers, vol. 1, p. 859-62.

"Evaluation of sensors for on-board diesel oil condition monitoring of U.S. Army ground equipment," SAE Technical Paper Series, 2005-01-1810, 2005 SAE World Congress, Detroit Michigan, Apr. 11-14, 2005.

"Determining Proper Oil and Filter Change Intervals: Can Onboard Automotive Sensors Help?", Practical Oil Analysis, Jan. 2004.

"Micromachine-based humidity sensors with integrated temperature sensors for signal drift compensation", Journal of Micromechanics and Microengineering, 13 (2003), pp. 620-627.

* cited by examiner

MICROELECTROMECHANICAL (MEM) FLUID HEALTH SENSING DEVICE AND FABRICATION METHOD

BACKGROUND OF THE INVENTION

1. Field of the Invention

This invention relates to the field of fluid health sensors, and particularly to microelectromechanical (MEM) devices and methods for determining the health of a fluid.

2. Description of the Related Art

Knowing the health and remaining useful life of a fluid is important in many applications. For example, fluids used in rotating machinery and hydraulic systems such as pumps, transmissions, turbines, etc., may fail or perform poorly when their operating fluids are at or near the end of their useful life. Systems damaged by the use of a degraded fluid may require costly repair or replacement, and are likely to result in unscheduled downtime.

The degradation of fluids such as liquid lubricants, engine oils, hydraulic fluids and the like, involves the simultaneous operation of a number of mechanical, chemical, and electrochemical processes. As such, no single physical metric is able to provide a high-confidence indication of fluid health or remaining useful life. Numerous methods have been employed to determine fluid health. For example, the conductivity of a fluid can be measured and plotted over time. The detection of an inflection point in the plotted measurement can indicate the end of the fluid's useful life. However, it can be difficult to detect the inflection point in the presence of noise, and there is significant variation in conductivity vs. time plots for different fluid types. As such, results obtained via this method alone can be unreliable.

Another approach is described in U.S. Pat. No. 6,852,216 to Moscaritolo et al. Here, a fluid filter employs a number of sensors to measure respective fluid parameters such as differential pressure, temperature, conductivity, viscosity, pH level, etc., with the results processed to determine the condition of the filter element. However, the described design is intended to determine the health of the filter element itself, rather than the fluid. Furthermore, each sensor is separately fabricated and packaged; providing a plurality of separate sensors in this way can be costly, require a unacceptably large amount of area, and may be unreliable.

There is a clear need for a small, inexpensive, reliable means of providing a high-confidence indication of fluid health.

SUMMARY OF THE INVENTION

A fluid health sensing device and method are presented which overcome the problems noted above, by providing a device capable of measuring multiple fluid parameters in a small, reliable sensor package.

The present fluid health sensing device comprises a viscosity sensor which provides an output that varies with the viscosity of a fluid in which it is immersed, and at least one other sensor which provides an output that varies with another predetermined parameter of the fluid. The viscosity sensor is preferably a microelectromechanical (MEM) device fabricated by means of a "deep etch" process described herein. The sensors are preferably integrated together on a common substrate, though they might also be fabricated separately, by prescribed means, and packaged together to form a hybrid device. A data processing means may be included which receives the sensor outputs and is arranged to provide one or more outputs indicative of the health and/or remaining useful life of the fluid.

Sensor types which may be part of the present device include, for example, a temperature sensor, a MEM electrochemical sensor, a MEM accelerometer, a MEM contact switch lubricity sensor, and/or an inductive metallic wear sensor. All of these additional sensors are preferably integrated together with the viscosity sensor on a common substrate using a common fabrication process. The data provided by the multiple sensors provides an accurate means of assessing fluid health, and the preferred co-fabrication of sensors results in a device which is small, low-cost and reliable.

Further features and advantages of the invention will be apparent to those skilled in the art from the following detailed description, taken together with the accompanying drawings.

DETAILED DESCRIPTION OF THE INVENTION

The present invention is directed to a device comprising two or more sensors which are capable of measuring respective parameters of a fluid in which they are immersed. The measured parameters are intended to provide an indication of the health of the fluid and/or its remaining useful life. The device includes a viscosity sensor and at least one other sensor type, such as temperature, electrochemical, lubricity, accelerometer, and/or wear sensors. The viscosity sensor is preferably a MEM device. The sensors may be integrated together on a common substrate, or may be fabricated by prescribed means on separate substrates and packaged together to form a hybrid device. A data processing means may be provided to receive the various sensor outputs and provide one or more outputs indicative of fluid health.

Figure 1:
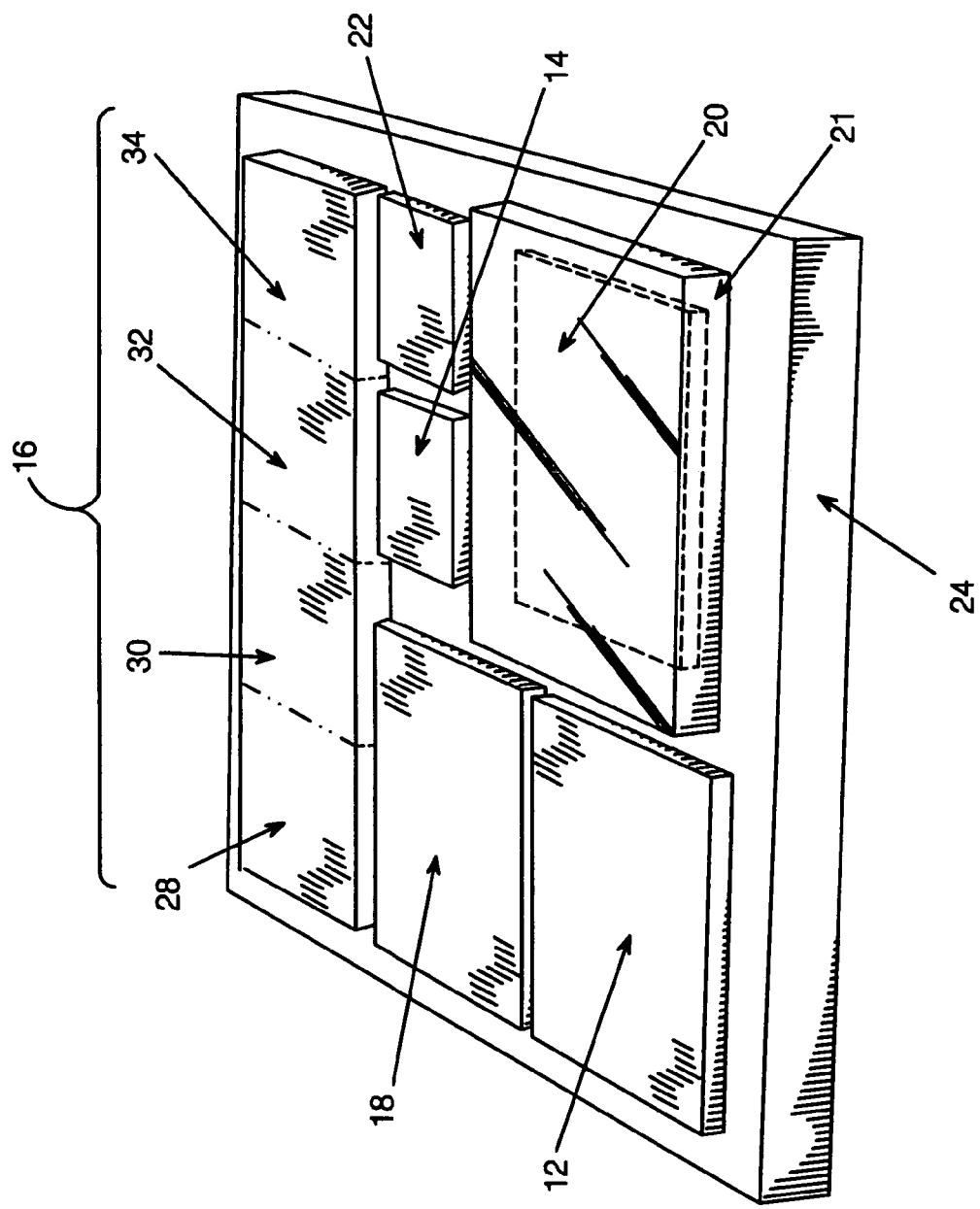
FIG. 1 is a functional block diagram of a MEM fluid health sensing device per the present invention.

A functional block diagram of a fluid health sensing device 10 is shown in FIG. 1. At a minimum, device 10 includes a viscosity sensor 12 and at least one other sensor type. As shown in FIG. 1, device 10 might also include a temperature sensor 14, an electrochemical sensor 16, a lubricity sensor 18, an accelerometer 20 contained within an enclosure 21 to isolate it from the fluid, and/or a wear sensor 22. Data processing circuitry 24 might also be included in device 10. Electrochemical sensor 16 could be arranged to measure one or more electrochemical properties of a fluid in which it is immersed; for example, separate sections of sensor 16 could be dedicated to the measurement of the fluid's pH (28), corrosivity (30), moisture content (32), total acid number (TAN) (34), total base number (TBN), oxidation state, conductivity, dielectric constant, etc.

The sensors may be integrated together on a common substrate, or may be fabricated on separate substrates and packaged together to form a hybrid device. If a hybrid device is formed, the viscosity sensor is preferably a MEM device fabricated in accordance with a "deep etch" process described below. Suitable MEM viscosity sensors are described, for example, in co-pending U.S. patent application Ser. Nos. 10/956,229, 11/222,721, and 11/224,798, which are assigned to the same assignee as the present case and are incorporated herein by reference.

A temperature sensor suitable for use with the present fluid health sensor would preferably comprise a long, thin lithographed trace of a material—typically a metal—which has a temperature coefficient of electrical resistance. The temperature sensor is immersed in the fluid, and by measuring the resistance of the trace, the fluid temperature can be determined. Such a temperature sensor could be fabricated using known means on the same substrate as the viscosity sensor, or on a separate substrate. Other, more process-intensive methods have been shown, but a long, thin lithographed metal trace is preferred due to its low cost and simplicity. Other temperature sensing devices could also be used; for example, a thin-film thermocouple made from two dissimilar metals, an RTD temperature sensor, or a diode temperature sensor could be located within the device package and used to provide an output which varies with the temperature of the fluid in which they are immersed.

As noted above, the preferred temperature sensor could be integrated with the viscosity sensor, or provided as an independent device. If integrated, the sensor could be a metal trace either on the viscosity sensor itself, or located at the periphery of the device die (but outside the device area).

Figure 2:
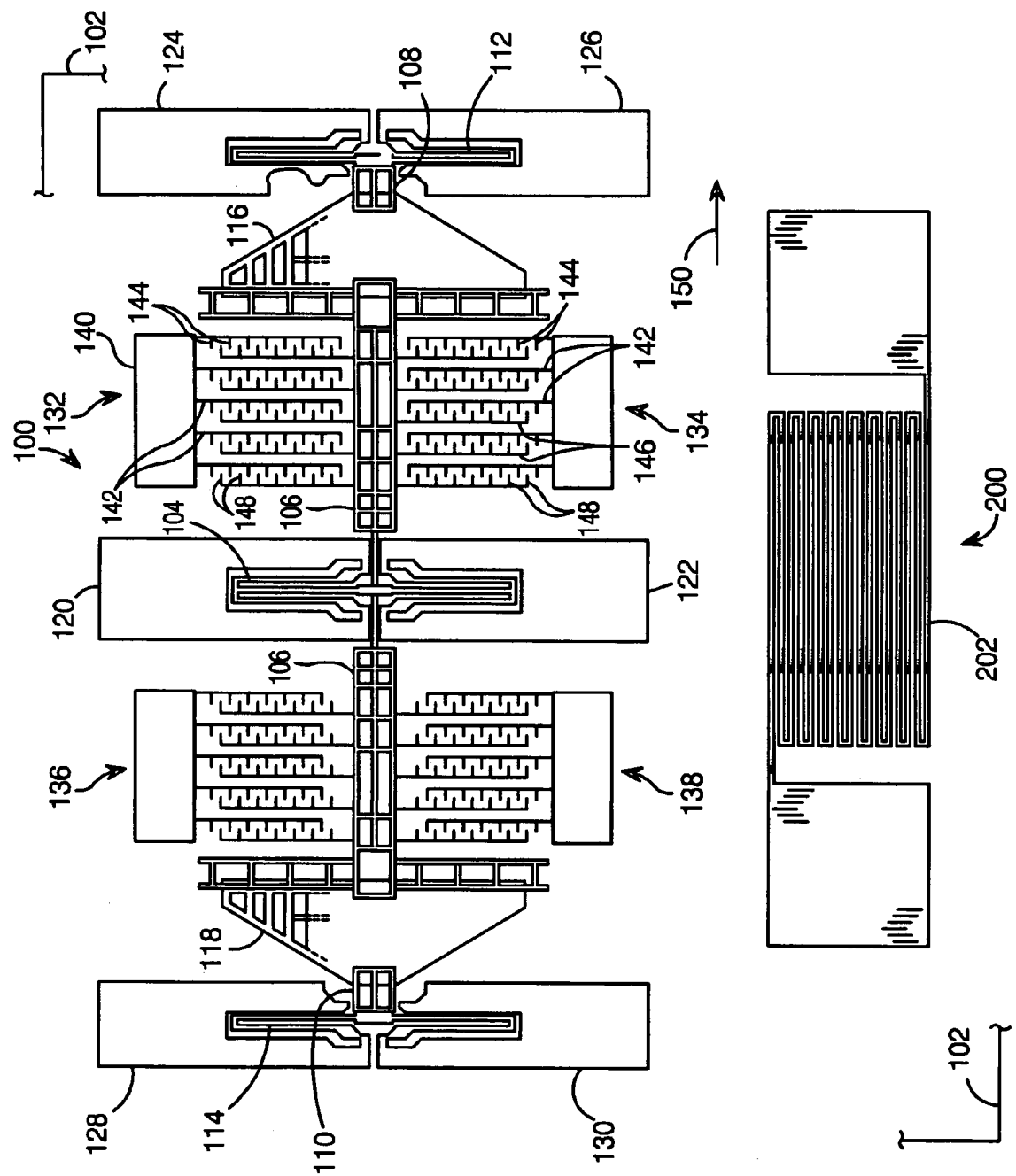
FIG. 2 is a plan view of a MEM viscosity sensor and a temperature sensor as might be employed in a MEM fluid health sensing device per the present invention.

One possible implementation of a MEM fluid health sensing device per the present invention, which includes a MEM viscosity sensor 100 and a preferred temperature sensor 200, is shown in FIG. 2. Exemplary MEM viscosity sensor 100 is disposed on a supporting substrate 102. In the embodiment shown, viscosity sensor 100 comprises a transverse, centrally located, compliant suspension 104 carrying a longitudinally-extending arm 106. The arm 106 includes transverse ends 108 and 110 coupled to compliant, electrically conductive suspension beams 112 and 114, via electrically insulating bridges 116 and 118, respectively, fabricated of, for example, silicon dioxide. Arm 106 and suspensions 104, 112 and 114 are mechanically coupled together to move longitudinally as a single unit with respect to the substrate 102, to form a motion actuator. Bridges 116 and 118, however, electrically isolate arm 106 from the electrically conductive suspensions 112 and 114. Suspension 104 is coupled at its opposed outer ends to anchors 120 and 122 affixed to substrate 102. Similarly, the outer ends of suspensions 112 and 114 are coupled to anchor pairs 124, 126 and 128, 130 respectively, affixed to substrate 102.

Sensor 100 further comprises comb sense capacitors 132, 134, 136 and 138 (also known as interdigitated capacitors) for providing signals to an external output circuit representing the displacement of the arm 106 from its rest position. The comb capacitors are identical; thus, only capacitors 132 and 134 will be described.

Comb capacitor 132 comprises a fixed member 140 having a plurality of cantilevered support members 142. Comb fingers 144, also referred to as comb plates, extend longitudinally from support members 142 to provide a large surface area for interacting with liquids. Capacitor 132 further comprises a plurality of members 146 cantilevered from the moveable arm 106. Comb fingers 148 extend longitudinally from members 146, and are configured to interleave with the comb fingers 144. As with comb fingers 144, moveable comb fingers 148 also provide a large surface area for interacting with liquids. Comb fingers 144 and 148 are made from electrically conductive materials. As such, comb fingers 144 and 148 form a capacitor whose capacitance varies with the amount of overlap between fingers 144 and 148.

Sensor 100 is coupled to a drive actuator, which causes transverse suspensions 112, 114 to move bridges 116, 118 longitudinally in the plane of FIG. 2 such that fingers 144 move parallel to fingers 148. The drive actuator can be, for example, an electrostatic, thermal, piezoelectric or Lorentz force actuator. Descriptions of actuators suitable for use in embodiments of the illustrated viscosity sensor can be found, for example, in U.S. Pat. No. 5,025,346 (electrostatic), and U.S. Patent Application Publication US 2004/0027029 (Lorentz).

Connections to one or more external circuits are made via anchors 124, 126, 128 and 130 carrying suspensions 112 and 114, to which the anchors are electrically connected. When actuated, arm 106 and the moveable portions of interconnected compliant suspensions 104, 112 and 114 move laterally as indicated by the arrow 150. For the specific embodiment of a device operating through Lorentz force actuation (and shown in FIG. 2), as the current flowing through one of the suspensions varies, the distance that arm 106 moves varies, thereby varying the overlap between comb fingers 144 and 148 and thus the capacitance between them.

If the capacitors are immersed in a liquid, the movement of comb fingers 144, 148 is dampened upon the application of a driving force from the drive actuator. The response time of the device, as determined through capacitive sensing, provides a measure of the fluid viscosity.

As noted above, temperature sensor 200 preferably comprises a long, thin lithographed trace of a material 202, typically a metal such as platinum, which has a temperature coefficient of electrical resistance. As noted above, temperature sensor 200 could be fabricated on substrate 102 with viscosity sensor 100, or on a separate substrate.

Alternatively, temperature sensor 200 could be fabricated directly on viscosity sensor 100, atop a fixed member such as anchor 128 or member 140, or on compliant beam 104 for example (not shown). This approach has the advantage of improving the accuracy of the device, due to the temperature sensor's close proximity to the viscosity sensor. However, fabricating the temperature sensor directly on the viscosity sensor may be more difficult than fabricating it separately, whether on the same substrate or a different substrate. Means of fabricating temperature sensors as described herein are well-known to those skilled in the art; details can be found, for example, in "Micromachine-based humidity sensors with integrated temperature sensors for signal drift compensation", Journal of Micromechanics and Microengineering, 13 (2003), pp. 620-627, and "MEMS Sensors for HVAC&R", ASHRAE Journal, May 2004, pp. 69-74.

As noted above, the present fluid health sensing device might employ viscosity sensor designs other than that shown in FIG. 2, and/or other temperature sensor types such as thin-film thermocouples, RTDs, or diode temperature sensors.

An electrochemical sensor as might be used with the present invention operates by monitoring electrical signals generated by chemical processes that occur when the sensor is exposed to the fluid being monitored. A conventional electrochemical sensor employs a planar set of interdigitated conductive traces on a surface. Various electrical measurements can be made between these two electrodes, such as DC resistance, current flow, AC impedance (at various frequencies), and capacitance (to extract the dielectric constant of the material between the electrodes). Chemical processes in the fluid (such as water content, acidity, oxidation, etc.) can alter these electrical properties, and thus their measurement provides indications of the ongoing chemical processes and state of the fluid.

Figure 3:
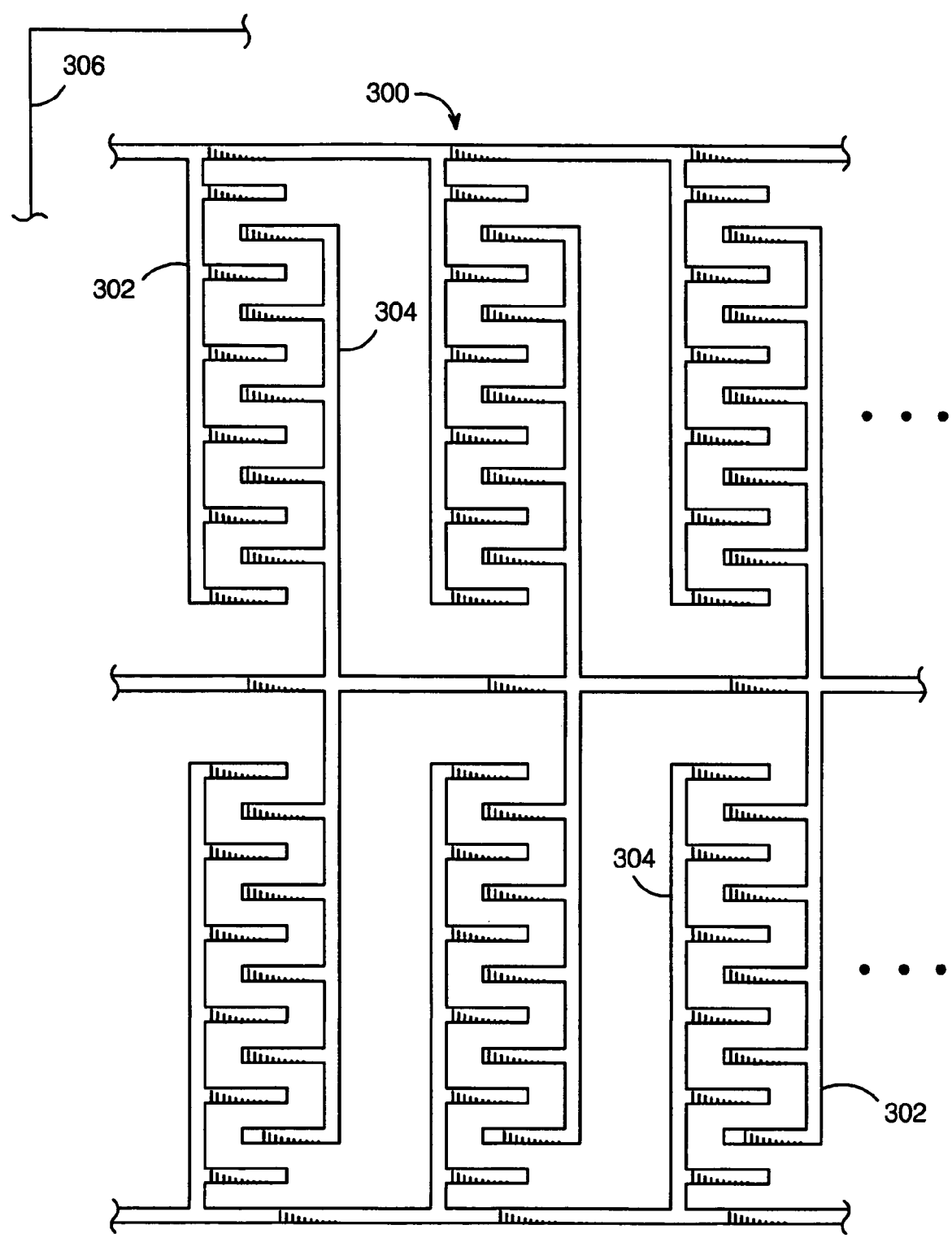
FIG. 3 is a simplified plan view of an exemplary electrochemical sensor as might be used with the present invention.

An electrochemical sensor as used in the present invention is preferably MEM-based; a simplified plan view of an exemplary electrochemical sensor embodiment 300 is shown in FIG. 3. Instead of planar electrodes, 3-dimensional interdigitated electrodes 302, 304 are formed on a substrate 306; the electrodes have a very high surface area and very close spacing, which serves to increase the capacitance, and hence the measurement sensitivity. Such sensors are preferably constructed using the "deep-etch" process referred to above; i.e., a silicon deep reactive ion etching (DRIE) process as described, for example, in U.S. Pat. No. 6,159,385, U.S. Patent Application Publication US 2004/0113513, and co-pending patent application Ser. No. 11/222,721, which are assigned to the same assignee as the present case and are incorporated herein by reference. This method involves the use of a silicon-on-insulator (SOI) wafer and a substrate. The SOI wafer, which includes a layer of doped silicon and an oxide layer, is bonded to the substrate to form a composite structure. The doped layer is patterned and etched to form the interdigitated electrode elements. In contrast to the viscosity sensor, the electrochemical sensor may be a static (non-movable) structure. As such, it would not require processing to undercut the adhesive and release the moveable elements. A metallization layer is typically deposited, masked and etched to provide electrical interconnections for the MEM device.

The preferred viscosity sensor is also "deep-etched" using the same DRIE process referenced above. As such, the viscosity and electrochemical sensors can be conveniently co-fabricated and integrated in close proximity. In general, a co-fabricated MEM-based electrochemical sensor would be a high aspect ratio silicon interdigitated comb structure. This would be a static device, i.e., with no moving parts, unreleased. The two sets of combs would be electrically isolated and would have electrical interconnects to access the signals. They may have surface coatings applied to facilitate the sensing response. Sensors of this sort are described, for example, in "Microfluidics Meets MEMS", Proceedings of the IEEE, Vol. 91, No. 6, June 2003, pp. 930-953.

The MEM-based sensors may be formed from a number of different materials. For example, single crystal silicon could be used as the structural material, with DRIE used to define the structures. Alternatively, polysilicon could be used as the structural material, with etching used to define the structures, or metal could be used as the structural material, with plating or etching used to define the structures. Additional micromachining and thin film processing would typically be employed to define elements such as the temperature sensor. Such processes would be well known to those skilled in the art of semiconductor or MEMS process technologies.

An accelerometer 20 might be incorporated into the present fluid health sensing device to identify vibrations that arise due to, for example, bearing wear in a motor assembly. This sensor would not be immersed in the fluid being monitored, but rather would be isolated from the fluid. A preferred accelerometer would consist of a MEM element tethered to a substrate with compliant flexures such that the MEM element is free to move under the influence of inertial forces. In operation, acceleration is determined by knowing the mass of the MEM element, and monitoring its motion using techniques such as capacitive sensing. The preferred accelerometer would look qualitatively like the preferred MEM viscosity sensor described above, with flexures and sense electrodes.

Figure 4:
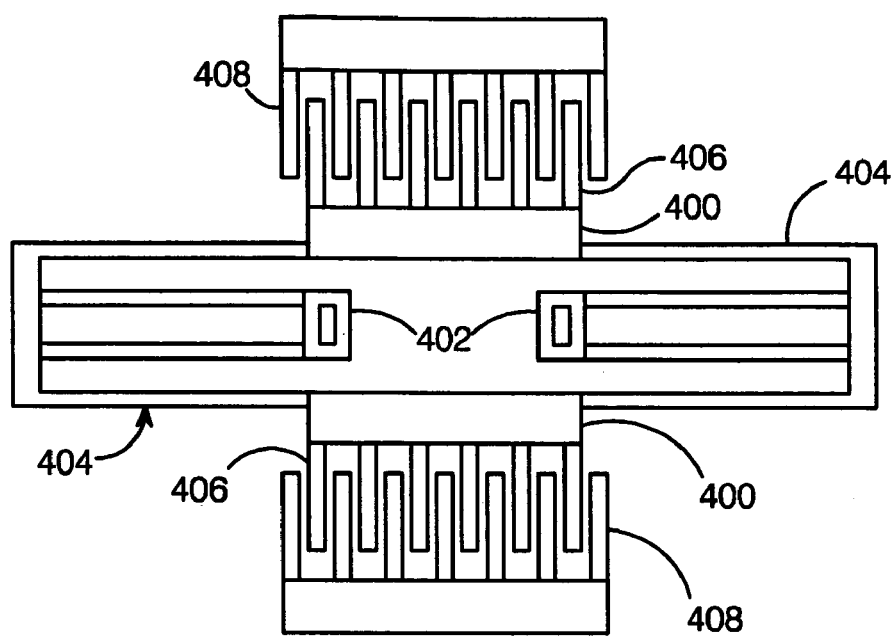
FIG. 4 is a simplified plan view of an exemplary accelerometer as might be used with the present invention.

A plan view of a simplified embodiment which illustrates the principles of a MEM accelerometer is shown in FIG. 4. Proof masses 400 are coupled to anchor members 402 via compliant flexures 404. A comb structure 406 is affixed to each proof mass, which is interdigitated with a fixed comb structure 408. Vibration causes the proof masses to move with respect to the anchor members, causing the capacitance between comb structures 406 and 408 to vary; the capacitance is sensed to determine acceleration. This type of device is widely described in the literature and commercially available. The accelerometer could be co-fabricated with the MEM viscosity sensor, but would require the application of a local capping to isolate it from the fluid. Additional information regarding accelerometers of this type can be found, for example, in "Presettable Micromachined MEMS Accelerometers", Proceedings of the 12th IEEE International Conference on Micro Electro Mechanical Systems (MEMS '99), "A Single-crystal Silicon 3-axis CMOS-MEMS Accelerometer," IEEE Sensors 2004, Vienna, Austria, October 2004, and "MEMS Sensors for HVAC&R", ASHRAE Journal, May 2004, pp. 69-74.

A contact switch lubricity sensor 18 might be incorporated into the present fluid health sensing device, to monitor the breakdown in the fluid's lubricating performance. In a preferred embodiment, the lubricity sensor employs a metal-metal contacting geometry similar to that of a MEM switch; the contacts are immersed in the fluid being monitored, which provides a degree of isolation between the metal contacts. To monitor the breakdown in lubricating performance, the voltage (or force) needed to make the switch contacts conduct is measured. The lubricity sensor is preferably co-fabricated using the same deep etch process as the viscosity sensor.

Figure 5:
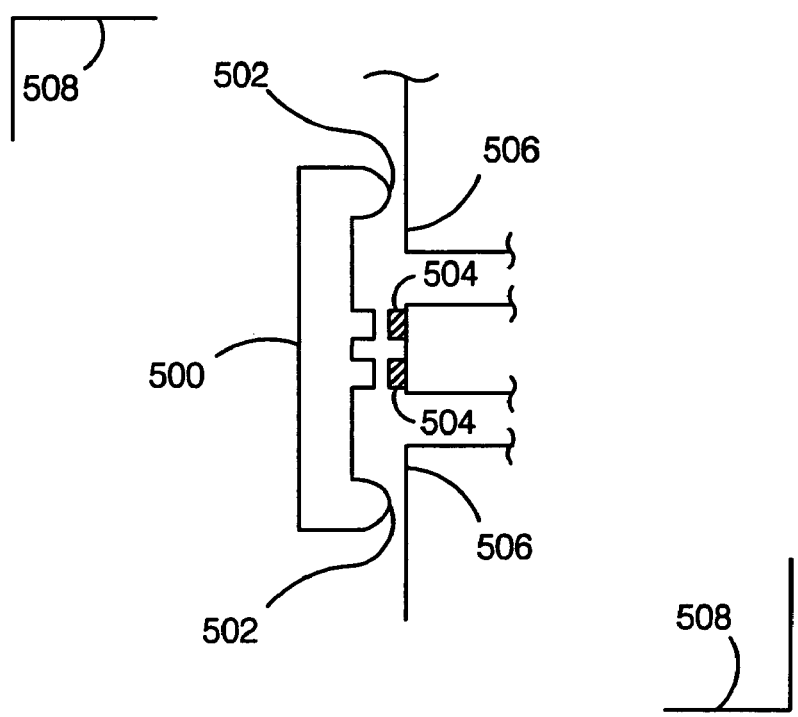
FIG. 5 is a simplified plan view of an exemplary lubricity sensor as might be used with the present invention.

A plan view of a simplified embodiment which illustrates the principles of a MEM lubricity sensor is shown in FIG. 5. An ohmic contact arm 500 having two contacts 502 (in this example), actuation electrodes 504, and structures 506 are fabricated on a substrate 508. In operation, the arm is immersed in the fluid being tested and actuated such that it moves laterally until contacts 502 reach structures 506. The resistance across the contacts is sensed. The force required to cause ohmic contact (i.e., the resistance vs. voltage curve) provides a measure of lubricating ability. Additional information regarding sensors of this type can be found, for example, in "A hybrid approach to low-voltage MEMS switches," TRANSDUCERS '03, 12th International Conference on Solid-State Sensors, Actuators and Microsystems, Digest of Technical Papers, Vol. 1, p. 859-62.

An inductive metallic wear sensor 22 might be incorporated to detect changes in the elemental and particulate content of the fluid. Such particulates may be generated by wear of metallic components in the system and may be indicative of degradation of the lubricant quality. Such a sensor would typically be implemented as a pair of plated micromachined 3D coils. The particulate-containing fluid would flow through one of the coils, and filtered, particulate-free fluid would flow through the other coil to provide a reference to compensate for changes in fluid temperature and other properties not related to particulate content. The coils are energized with an AC current, and the relative inductance of the coils is monitored over time to provide an indication of the fluid's elemental and particulate content. The wear sensor is preferably co-fabricated with the other sensors. While it may require fabrication processes other than Si deep etching (such as metal plating), these processes would be compatible with the fabrication processes used for the other sensors, permitting integration and co-fabrication. When the deep etch process is used, the coils could be formed on top of the Si device layer using thick resist and metal plating processes. Alternatively, the coils could be embedded into the Si device layer, forming them through etch and plating processes. The Si around the coil would be etched away to leave the metal coil. Additional information regarding sensors of this type can be found, for example, in U.S. Pat. Nos. 4,176,545 and 5,444,367.

The present fluid health sensing device may also include a data processing means 24, which would be arranged to receive the outputs of each of the device's sensors and provide one or more outputs indicative of the health of the subject fluid. The output of each parameter sensor varies with one or more characteristics of the fluid being monitored, such as its viscosity, pH, particulate content, etc. These outputs are preferably processed in accordance with algorithms developed to provide an indication of fluid health based on the measured characteristics. Algorithms of this sort are known, and are described, for example, in "Evaluation of sensors for on-board diesel oil condition monitoring of U.S. Army ground equipment," SAE Technical Paper Series, 2005-01-1810, 2005 SAE World Congress, Detroit Mich., Apr. 11-14, 2005, "Determining Proper Oil and Filter Change Intervals: Can Onboard Automotive Sensors Help?", Practical Oil Analysis, January 2004, and U.S. Pat. Nos. 6,644,095 and 6,463,796.

The data processing means might be co-fabricated with the other sensors on a common substrate, fabricated on a separate substrate which interconnects to the sensors, or be entirely separate from the present fluid health sensing device. When the aforementioned deep etch process is used to form the MEM-based sensors, the data processing circuitry would typically be fabricated on a separate wafer or substrate.

A fluid health sensing device as described herein can be utilized in a variety of situations in which measurements determining the health of a liquid are desired. For example, the device could be installed in the oil tank of a vehicle or machine, or in a separate testing apparatus to which liquid samples are brought. The device could be used for in-situ fluid health monitoring, immersed, for example, in the working fluids of pumps, turbines, engines, etc. They might also be advantageously employed in fluid processing applications, such as in the chemical or food processing industries.

Note that the viscosity sensor shown in FIG. 2 is merely exemplary. It is only required that the present device include a viscosity sensor and at least one other sensor, which are either co-fabricated on a common substrate or separately fabricated in accordance with means described herein.

While particular embodiments of the invention have been shown and described, numerous variations and alternate embodiments will occur to those skilled in the art. Accordingly, it is intended that the invention be limited only in terms of the appended claims.

We claim:

1. A microelectromechanical (MEM) fluid health sensing device, comprising:
   a MEM viscosity sensor arranged to, when immersed in a fluid, provide an output which varies with the viscosity of said fluid; and
   a temperature sensor arranged to, when immersed in said fluid, provide an output which varies with the temperature of said fluid, said viscosity and said temperature sensor integrated together on a common substrate;
   wherein said temperature sensor comprises a lithographed trace of a material having a known temperature coefficient of electrical resistance.

2. The device of claim 1, wherein said temperature sensor is fabricated directly on said MEN viscosity sensor.

3. A microelectromechanical (MEM) fluid health sensing device, comprising:
   a MEM viscosity sensor arranged to, when immersed in a fluid, provide an output which varies with the viscosity of said fluid; and
   a MEM electrochemical sensor arranged to, when immersed in said fluid, provide an output which varies with one or more electrochemical properties of said fluid, said viscosity and said MEM electrochemical sensor integrated together on a common substrate;
   wherein said electrochemical sensor comprises a plurality of static interdigitated electrodes.

4. A microelectromechanical (MEM) fluid health sensing device, comprising:
   a MEM viscosity sensor arranged to, when immersed in a fluid, provide an output which varies with the viscosity of said fluid; and
   a MEM accelerometer arranged to provide an output which varies with vibration, said viscosity and said MEM accelerometer integrated together on a common substrate;
   wherein said MEM accelerometer is locally capped to isolate it from said fluid.

5. A microelectromechanical (MEM) fluid health sensing device, comprising:
   a MEM viscosity sensor arranged to, when immersed in a fluid, provide an output which varies with the viscosity of said fluid; and
   a MEM contact switch lubricity sensor arranged to, when immersed in said fluid, provide an output which varies with said fluid's lubricating performance.

6. The device of claim 5, wherein said lubricity sensor includes a pair of switch contacts and said output varies with the applied voltage or force needed to make said switch contacts conduct.

7. A microelectromechanical (MEM) fluid health sensing device, comprising:
   a MEM viscosity sensor arranged to, when immersed in a fluid, provide an output which varies with the viscosity of said fluid; and
   an inductive metallic wear sensor arranged to, when immersed in said fluid, provide an output which varies with said fluid's elemental and particulate content.

8. The device of claim 7, wherein said wear sensor includes first and reference plated micromachined 3D coils, said first coil containing fluid to be sensed and said reference coil containing filtered fluid, said coils arranged such that said output varies with the relative inductance of the coils when said coils are energized with an AC current.

9. A microelectromechanical (MEM) fluid health sensing device, comprising:
   a MEM viscosity sensor arranged to, when immersed in a fluid, provide an output which varies with the viscosity of said fluid; and
   at least one other sensor arranged to, when immersed in said fluid, provide an output which varies with a predetermined parameter of said fluid, said viscosity and said at least one other sensor integrated together on a common substrate;

wherein said MEM viscosity sensor includes movable and stationary elements, said sensor comprising a silicon-on-insulator (SOI) wafer which includes a silicon device layer, said device layer etched using a deep reactive ion etch (DRIE) to form said movable and stationary elements.

10. A microelectromechanical (MEM) fluid health sensing device, comprising:
a MEM viscosity sensor arranged to sense the viscosity of a fluid in which it is immersed and to provide an output which varies with said viscosity, comprising:
a semiconductor wafer;
a substrate bonded to said wafer and thereby forming a composite structure, portions of said composite structure patterned and etched to form first and second sets of conductive plates spaced apart from each other and having respective parallel surface areas, said first set of plates arranged to interleave with said second set of plates such that their surface areas at least partially overlap to produce a capacitance, one of said sets of plates being a movable element and the other of said sets of plates being a stationary element; and
a drive means for displacing said movable element relative to said stationary element, said viscosity sensor arranged to, when immersed in said fluid, provide an output which varies with the viscosity of said fluid; and
at least one other sensor arranged to, when immersed in said fluid, provide an output which varies with a parameter of said fluid;
said MEM viscosity sensor and said at least one other sensor packaged together in a common housing.

11. The device of claim 10, wherein said at least one other sensor comprises a MEM electrochemical sensor arranged to, when immersed in said fluid, provide an output which varies with one or more electrochemical properties of said fluid.

12. The device of claim 11 wherein said electrochemical properties comprise pH, corrosivity, moisture content, Total Acid Number (TAN), Total Base Number (TBN), oxidation state, conductivity, and/or dielectric constant.

13. The device of claim 10, wherein said at least one other sensor comprises a MEM accelerometer arranged to provide an output which varies with vibration.

14. The device of claim 13, wherein said accelerometer comprises:
a least one proof mass;
at least one anchor member;
compliant flexures coupled between respective ones of said anchor members and proof masses;
a movable comb structure affixed to each of said proof masses; and
fixed comb structures interdigitated with respective ones of said movable comb structures, such that said proof masses move with respect to said anchor members and the capacitance between said movable and fixed comb structures varies with acceleration.

15. The device of claim 10, wherein said movable element is arranged to move in said fluid such that it is subjected to a predominately shear force.

16. The device of claim 10, wherein said MEM viscosity sensor is arranged such that said drive means displaces said movable element laterally relative to said stationary element.

17. The device of claim 10, wherein said MEM viscosity sensor is arranged such that said drive means displaces said movable element vertically relative to said stationary element.

18. The device of claim 10, further comprising an organic adhesive which bonds said substrate to said wafer.

19. The device of claim 10, wherein said wafer and substrate have respective bonding pads which are aligned and mechanically connected such that a thermocompression bond is formed to effect the bonding of said wafer to said substrate.

20. The device of claim 19, wherein said bonding pads are gold (Au) and said thermocompression bond is an Au-Au thermocompression bond.

21. The device of claim 10, wherein said wafer and substrate have respective bonding pads which are aligned and mechanically connected such that an anodic bond is formed to effect the bonding of said wafer to said substrate.

22. The device of claim 10, wherein said semiconductor wafer is a silicon-on-insulator (SOI) wafer.

23. The device of claim 10, wherein said MEM viscosity sensor and said at least one other sensor are separately fabricated and packaged together in said common housing to form a hybrid device.

24. The device of claim 10, wherein said MEM viscosity sensor and said at least one other sensor are integrated together on a common substrate.

25. The device of claim 10, further comprising a data processing means which receives said sensor outputs and is arranged to provide one or more outputs indicative of the health of said fluid.

26. The device of claim 10, wherein said at least one other sensor comprises one or more sensors selected from a group consisting of:
a MEM electrochemical sensor arranged to, when immersed in said fluid, provide an output which varies with one or more electrochemical properties of said fluid;
a MEM accelerometer arranged to provide an output which varies with vibration;
a MEM contact switch lubricity sensor arranged to, when immersed in said fluid, provide an output which varies with said fluid's lubricating performance; or
a inductive metallic wear sensor arranged to, when immersed in said fluid, provide an output which varies with said fluid's elemental and particulate content.

27. The device of claim 10, further comprising a sensing means for sensing said amount of overlap.

28. The device of claim 10, wherein said drive means is selected from a group consisting of an electrostatic actuator, thermal actuator, Lorentz force actuator, or piezoelectric actuator, said actuator coupled to said movable element.

29. A method of determining the health of a fluid, comprising:
providing a microelectromechanical (MEM) fluid health sensing device, comprising:
a MEM viscosity sensor arranged to, when immersed in a fluid, provide an output which varies with the viscosity of said fluid, said MEM viscosity sensor comprising:
a semiconductor wafer;
a substrate bonded to said wafer and thereby forming a composite structure, portions of said composite structure patterned and etched to form first and second sets of conductive plates spaced apart from each other and having respective parallel surface areas, said first set of plates arranged to interleave with said second set of plates such that their surface areas at least partially overlap to produce a capacitance, one of said sets of plates being a movable element and the other of said sets of plates being a stationary element; and a drive means for displacing said movable element relative to said stationary element; and at least one other sensor arranged to, when immersed in said fluid, provide an output which varies with a predetermined parameter of said fluid, said viscosity and said at least one other sensor integrated together on a common substrate;

immersing said sensors in a fluid, the health of which is to be determined; and processing said sensor outputs to provide one or more outputs indicative of the health of said fluid.

30. The method of claim 29, wherein said at least one other sensor comprises a temperature sensor arranged to, when immersed in said fluid, provide an output which varies with the temperature of said fluid.

31. The method of claim 29, wherein said at least one other sensor comprises a MEM electrochemical sensor arranged to, when immersed in said fluid, provide an output which varies with one or more electrochemical properties of said fluid.

32. The method of claim 29, further comprising displacing said movable element laterally relative to said stationary element such that it is subjected to a predominately shear force.

33. The method of claim 29, further comprising displacing said movable element vertically relative to said stationary element such that it is subjected to a predominately shear force.

34. The method of claim 29, wherein said MEM viscosity sensor further comprises:

a sensing means for sensing said amount of overlap; said method further comprising:

operating said drive means to displace said movable element relative to said stationary element; and operating said sensing means to sense said amount of overlap.

35. A method of fabricating a microelectromechanical (MEM) fluid health sensing device, comprising:

providing a semiconductor wafer;

providing a substrate;

bonding said wafer and substrate together to form a composite structure; and patterning and etching portions of said composite structure to form at least two sensors which, when immersed in a fluid the health of which is to be determined, provide respective outputs which vary with one or more parameters of said fluid.

36. The method of claim 35, wherein at least one of said sensors is a micro-electromechanical (MEM) sensor.

37. The method of claim 35, wherein said MEM sensor is arranged to sense the viscosity of said fluid.

38. The method of claim 37, wherein said patterning and etching of said composite structure form a stationary element and a movable element such that said movable element is mechanically coupled to said stationary element, said movable element and said stationary element conductive and at least partially overlapping so as to produce a capacitance which varies with the amount of overlap.

39. The method of claim 38, wherein said stationary element and a movable element comprise a first set and a second set of conductive plates, respectively, said sets of conductive plates spaced apart from each other and having respective parallel surface areas, said first set of plates arranged to interleave with said second set of plates such that their surface areas at least partially overlap to produce said capacitance.

40. A method of fabricating a microelectromechanical (MEM) fluid health sensing device which includes at least one MEM sensor, each of which has a stationary element and a movable element displaceable relative to the stationary element, comprising:

providing a silicon-on-insulator (SCI) wafer which includes a silicon handle layer and a silicon device layer;

providing a substrate;

etching a recessed area into said substrate;

bonding said wafer to said substrate to form a composite structure;

removing said silicon handle layer from the SOI wafer to expose said silicon device layer;

patterning and etching portions of said composite structure to define the stationary and movable elements of at least one MEM sensor, and at least one other sensor;

depositing, patterning and etching one or more metallization layers on said composite structure to provide electrical interconnections for said sensors; and releasing said movable elements;

said sensors arranged to provide respective outputs which vary with one or more parameters of a fluid in which they are immersed.

41. The method of claim 40, wherein said device layer is etched using a deep reactive ion etch (DRIE).

42. The method of claim 40, wherein said bonding of said wafer and substrate is effected with an organic adhesive.

43. The method of claim 40, wherein said bonding of said wafer and substrate comprises:

patterning one or more bonding pads on said wafer;

patterning one or more bonding pads on said substrate such that said substrate's bonding pads can be aligned with said wafer's bonding pads;

aligning said wafer's bonding pads with said substrate's bonding pads; and mechanically connecting the bonding pads of said wafer and substrate to produce a mechanical bond which effects said bonding.

44. The method of claim 43, wherein said mechanical bond is a thermocompression bond.

45. The method of claim 43, wherein said mechanical bond is an anodic bond.

46. The method of claim 40, wherein said silicon device layer comprises single crystal silicon.

47. The method of claim 40, wherein said metallization layers comprise a conductive refractory material.

* * * * *

UNITED STATES PATENT AND TRADEMARK OFFICE
CERTIFICATE OF CORRECTION

PATENT NO. : 7,328,604 B2
APPLICATION NO. : 11/234015
DATED : February 12, 2008
INVENTOR(S) : Jeffrey F. DeNatale et al.

It is certified that error appears in the above-identified patent and that said Letters Patent is hereby corrected as shown below:

- Column 12, Claim 40, Line 17, is written as: "providing a silicon-on-insulator (SCI) wafer which". It should read as: "providing a silicon-on-insulator (SOI) wafer which".

Signed and Sealed this

Ninth Day of March, 2010

David J. Kappos
*Director of the United States Patent and Trademark Office*